(12) United States Patent
Nakano

(10) Patent No.: US 7,541,491 B2
(45) Date of Patent: Jun. 2, 2009

(54) GENE INVOLVED IN GROWTH-PROMOTING FUNCTION OF ACETIC ACID BACTERIA AND USES THEREOF

(75) Inventor: Shigeru Nakano, Aichi (JP)

(73) Assignee: Mitsukan Group Corporation, Handa-shi (JP)

( * ) Notice: Subject to any disclaimer, the term of this patent is extended or adjusted under 35 U.S.C. 154(b) by 80 days.

(21) Appl. No.: 10/561,834

(22) PCT Filed: Jun. 16, 2004

(86) PCT No.: PCT/JP2004/008797

§ 371 (c)(1),
(2), (4) Date: Dec. 22, 2005

(87) PCT Pub. No.: WO2005/001095

PCT Pub. Date: Jan. 6, 2005

(65) Prior Publication Data

US 2006/0228445 A1    Oct. 12, 2006

(30) Foreign Application Priority Data

Jun. 26, 2003  (JP) ............................. 2003-183047

(51) Int. Cl.
*C07C 51/16* (2006.01)
*C12N 15/00* (2006.01)
*C12N 1/20* (2006.01)
*C07H 21/02* (2006.01)

(52) U.S. Cl. ................. 562/536; 435/252.3; 435/320.1; 536/23.1

(58) Field of Classification Search ................. 562/536; 435/252.3, 320.1; 536/23.1
See application file for complete search history.

(56) References Cited

U.S. PATENT DOCUMENTS 5,914,257 A    6/1999  Fukaya et al.

FOREIGN PATENT DOCUMENTS

| CN | 2437691 Y | 7/2001 |
|---|---|---|
| GB | 781584 A | 8/1957 |
| JP | 53-96395 A | 8/1978 |
| JP | 61-205475 A | 9/1986 |
| JP | 2-2364 A | 1/1990 |
| JP | 2-53477 A | 2/1990 |
| JP | 3-219878 A | 9/1991 |
| JP | 6-90733 A | 4/1994 |
| JP | 2003-289867 A | 10/2003 |
| JP | 2003-289868 A | 10/2003 |
| JP | 2004-121021 A | 4/2004 |
| WO | WO-03/078622 A1 | 9/2003 |
| WO | WO-03/078635 A | 9/2003 |

OTHER PUBLICATIONS

Bowie et al. "Deciphering the message in protein sequences: tolerance to amino acid substitutions" Science, vol. 247, pp. 1306-1310, 1990.*
Ngo et al. "Computational complexity, protein structure prediction and the levinthal paradox", in "The Protein Folding Problem and Tertiary Structure Prediction," 1994, Merz et al. (ed.), Birkhauser, Boston, MA, pp. 433 and 492-495.*
Accession CP000009_19/c from Gluconobacter oxydans (see SEQ ID No. 2 sequence alignment, result 2, database: GenEmbl).*
Schuller G. et al., Int J Syst Evol Microbiol., 2000, vol. 50, No. 6, pp. 2013 to 2020.
Fukaya M. et al., J Bacteriol., 1990, vol. 172, No. 4, pp. 2096 to 2104.
Steiner et al., Applied and Environmental Microbiology, vol. 67, No. 12, pp. 5474-5481, (2001). XP-002358349.

* cited by examiner

*Primary Examiner*—Maryam Monshipouri
(74) *Attorney, Agent, or Firm*—Birch, Stewart, Kolasch & Birch, LLP

(57) ABSTRACT

The present invention provides a gene involved in the growth-promoting function of acetic acid bacteria and a microorganism containing the gene. In particular, the present invention provides a method for enhancing the growth-promoting function of acetic acid bacteria and a method for efficiently producing vinegar containing acetic acid at a high concentration in a short time using such acetic acid bacteria having an enhanced growth-promoting function.

5 Claims, 4 Drawing Sheets

FIG. 3

| | | |
|---|---|---|
| MetArgLeuArgMetValLeuLeuAlaThr | AlaLeuGlyAlaAlaProPheAlaThrAla | 20 |
| MetAlaThrThrIleThrGlyProTyrVal | AspIleGlyGlyGlyTyrAspLeuThrGln | 40 |
| ThrGlnHisAlaHisGlyPheAspLysAsn | GlnTyrGluAsnAsnAlaAsnThrAlaGly | 60 |
| TyrLeuAspAlaThrAspAsnAlaArgLeu | LeuLysGluAlaHisSerArgGluArgMet | 80 |
| GluHisGlyAspGlyTrpThrGlyPheAla | ThrPheGlyTrpGlyPheGlyAsnGlyLeu | 100 |
| ArgAlaGluIleGluGlyAspTyrAsnTrp | SerAlaLeuThrGlyTyrAsnSerValSer | 120 |
| GlySerAlaTyrGlyAsnAsnHisGlnSer | GlyLysSerSerGlySerAspArgSerTyr | 140 |
| GlyGlyPheValAsnValLeuTyrAspIle | AspLeuLysArgLeuPheAsnIleAspVal | 160 |
| ProValThrProPheValGlyValGlyAla | GlyTyrLeuTrpGlnAsnValAspAlaSer | 180 |
| ThrSerValThrArgTyrLeuAsnValArg | GlnAsnGlyThrAsnGlySerPheAlaTyr | 200 |
| GlnGlyMetValGlyAlaAlaTyrAspIle | ProGlyValProGlyLeuGlnMetThrThr | 220 |
| GluTyrArgMetIleGlyGlnValGluSer | PheAlaMetGlyAsnIleSerGlnThrGly | 240 |
| GlyGlyAspArgThrLeuSerTyrAspHis | ArgPheAsnHisGlnPheIleValGlyVal | 260 |
| ArgTyrAlaPheAsnHisAlaProProPro | ProProProAlaProAlaValAlaProPro | 280 |
| AlaProSerAlaAlaArgThrTyrLeuVal | PhePheAspTrpAspGlyAlaValLeuThr | 300 |
| AspArgAlaArgGlyIleValAlaGluAla | AlaGlnAlaSerThrHisValGlnThrThr | 320 |
| ArgIleGluValAsnGlyTyrThrAspAsn | ThrSerAlaHisProGlyProArgGlyGlu | 340 |
| LysTyrAsnLeuGlyLeuSerMetArgArg | AlaAspSerValLysAlaGluLeuIleArg | 360 |
| AspGlyValProAlaGlyGlyIleAspIle | HisTrpTyrGlyGluAlaHisProLeuVal | 380 |
| ValThrGlnProAspThrArgGluProGln | AsnArgArgValGluIleIleLeuHis | 399 |

SEQUENCE LISTING

```
<160> NUMBER OF SEQ ID NOS: 7

<210> SEQ ID NO 1
<211> LENGTH: 2352
<212> TYPE: DNA
<213> ORGANISM: Gluconacetobacter entanii

<400> SEQUENCE: 1
gatccagcca tggacaggtg cgggcaggtt tcccggcatt cccgtttcag ctccttcccg      60
ctggcattgc gataatggcc tcaggccaac tgtatcaaca tgcatcaggc cagtgtggaa     120
catgccccca tctccacaaa caagaaggcg tctgatcaag tatctttaag gacgggaata     180
tgcgtcttcg catggtatta ctggcgactg cacttggcgc agcgccattc gccaccgcaa     240
tggccacgac gattacaggg ccatatgtcg atatcggtgg cgggtatgac ctgacccaga     300
cccagcatgc ccatggcttt gacaagaacc agtacgaaaa caacgcaaat acggccgggt     360
atcttgatgc aacggacaac gcccgcctgc tgaaggaagc ccattcacgc gaacgcatgg     420
aacatggcga tggctggacc ggcttcgcca cgttcggctg ggggttcggc aacggcctgc     480
gcgcggaaat cgagggggat tacaactggt ccgccctgac cggctacaac tcggtttccg     540
gttccgccta tggcaacaat catcagagcg gcaagtccag cggcagcgac cggtcctatg     600
gcggattcgt caacgtcctg tatgacatcg acctcaagcg cctgtttaac attgacgtgc     660
ccgtgacacc attcgtcggc gttggcgccg gttacctgtg gcagaacgtg gatgccagca     720
catccgtgac ccgctacctg aacgtgcgcc agaacggcac gaatggcagc ttcgcctatc     780
```

```
agggcatggt cggcgcggcc tatgacatcc ccggtgtgcc cggcctgcag atgaccaccg    840
ataccgcat  gatcggacag gtggaatcct tcgccatggg caatatcagc cagactggcg    900
gcggtgaccg cacgctgagc tacgaccatc gcttcaacca tcagttcatc gtcggcgtcc    960
gctacgcctt caaccacgcg ccaccgccgc cgccgcccgc gcccgccgtg cgccccctg    1020
cccccagcgc ggcccgtacc tatctcgtat tctttgactg ggatggcgcg gtcctgaccg    1080
atcgcgcgcg cgggatcgtg gcggaagcgg cgcaggcttc cacgcatgtc cagacgaccc    1140
gtatcgaagt caacggctat accgacaaca cctcggccca ccccggacca cgtgggggaga   1200
agtataacct tggcctgtcc atgcggcgcg cagacagcgt gaaggctgaa ctgatccgtg    1260
acggcgtacc cgctggcggc atcgacatcc actggtatgg cgaagcccat ccgctggtgg    1320
tcacccagcc cgatacgcgt gagccgcaga accgtcgcgt cgaaatcatc ctgcactgac    1380
gacacatact gcaataaatt gataaatagg ctttttttaca aggggcgca caggatgcgc    1440
ccctttccat atcgaatcgt tccgatgcat cacaggccat gaatcagccc ttccgtttcc    1500
ggcactgtcc tatgcaaaat aaaggggtct attatcggac ttcaaaaaaa accttataaa    1560
atcgggactt tttacggaat acctccaaat gccctgaaag atatgtgtgt ttttcgccac    1620
acctcgttgg catgcggcat tttgcccatt ctcaagtcgg tccagacagg ctaatcccgc    1680
atcatagctt gcgggtaatc tcaggctgcc ctgtatcggg gcaaatccat tgcccgacca    1740
caagataggg ctctgccctg caacaacaga gttaaggact gaaacatgcg tcttcgcgca    1800
gcgttactgg ctaccagcct gctggcagcg gcaccgttcg ccgccaaagc cacgaccatc    1860
accggcccgt atgtcgatat cggcggcggc tacaacctga cccagaccca gcacgggcac    1920
tttgccgaca cggaagacgg cccgggccgc gaaaagctgg gccaccgtca tggctggacc    1980
ggcttcggcg cattcggctg gggcttcggc aacggtctgc gtgctgaaat cgagggcgac    2040
tacaactggt ccgaaatcta cagcaagtcc cgtaatgaca agggcagcga ccgctcctat    2100
ggcggtttcg tcaacgtgct gtatgacatc gacctgaagc gtctgttcaa catcgacgtg    2160
cccgtcaccc cgttcgtcgg tgtcggcgcc ggctacctgt ggcagaacgc acatgacgtg    2220
agcgtgggca acagccccgg tcgcagcctg agcggcacca agggcggctt cgcctaccag    2280
ggcatcgtcg gtcggcccta cgacatcccc ggtgtccctg gcctgcagat gaccaccgaa    2340
taccgcatga tc                                                        2352
```

<210> SEQ ID NO 2
<211> LENGTH: 399
<212> TYPE: PRT
<213> ORGANISM: Gluconacetobacter entanii

<400> SEQUENCE: 2

Met Arg Leu Arg Met Val Leu Leu Ala Thr Ala Leu Gly Ala Ala Pro
1               5                   10                  15

Phe Ala Thr Ala Met Ala Thr Thr Ile Thr Gly Pro Tyr Val Asp Ile
                20                  25                  30

Gly Gly Gly Tyr Asp Leu Thr Gln Thr Gln His Ala His Gly Phe Asp
            35                  40                  45

Lys Asn Gln Tyr Glu Asn Asn Ala Asn Thr Ala Gly Tyr Leu Asp Ala
        50                  55                  60

Thr Asp Asn Ala Arg Leu Leu Lys Glu Ala His Ser Arg Glu Arg Met
65                  70                  75                  80

Glu His Gly Asp Gly Trp Thr Gly Phe Ala Thr Phe Gly Trp Gly Phe

-continued

```
                    85                  90                  95
Gly Asn Gly Leu Arg Ala Glu Ile Glu Gly Asp Tyr Asn Trp Ser Ala
            100                 105                 110
Leu Thr Gly Tyr Asn Ser Val Ser Gly Ser Ala Tyr Gly Asn Asn His
        115                 120                 125
Gln Ser Gly Lys Ser Ser Gly Ser Asp Arg Ser Tyr Gly Gly Phe Val
    130                 135                 140
Asn Val Leu Tyr Asp Ile Asp Leu Lys Arg Leu Phe Asn Ile Asp Val
145                 150                 155                 160
Pro Val Thr Pro Phe Val Gly Val Gly Ala Gly Tyr Leu Trp Gln Asn
                165                 170                 175
Val Asp Ala Ser Thr Ser Val Thr Arg Tyr Leu Asn Val Arg Gln Asn
            180                 185                 190
Gly Thr Asn Gly Ser Phe Ala Tyr Gln Gly Met Val Gly Ala Ala Tyr
        195                 200                 205
Asp Ile Pro Gly Val Pro Gly Leu Gln Met Thr Thr Glu Tyr Arg Met
    210                 215                 220
Ile Gly Gln Val Glu Ser Phe Ala Met Gly Asn Ile Ser Gln Thr Gly
225                 230                 235                 240
Gly Gly Asp Arg Thr Leu Ser Tyr Asp His Arg Phe Asn His Gln Phe
                245                 250                 255
Ile Val Gly Val Arg Tyr Ala Phe Asn His Ala Pro Pro Pro Pro
            260                 265                 270
Pro Ala Pro Ala Val Ala Pro Ala Pro Ser Ala Ala Arg Thr Tyr
        275                 280                 285
Leu Val Phe Phe Asp Trp Asp Gly Ala Val Leu Thr Asp Arg Ala Arg
    290                 295                 300
Gly Ile Val Ala Glu Ala Ala Gln Ala Ser Thr His Val Gln Thr Thr
305                 310                 315                 320
Arg Ile Glu Val Asn Gly Tyr Thr Asp Asn Thr Ser Ala His Pro Gly
                325                 330                 335
Pro Arg Gly Glu Lys Tyr Asn Leu Gly Leu Ser Met Arg Arg Ala Asp
            340                 345                 350
Ser Val Lys Ala Glu Leu Ile Arg Asp Gly Val Pro Ala Gly Gly Ile
        355                 360                 365
Asp Ile His Trp Tyr Gly Glu Ala His Pro Leu Val Val Thr Gln Pro
    370                 375                 380
Asp Thr Arg Glu Pro Gln Asn Arg Val Glu Ile Ile Leu His
385                 390                 395

<210> SEQ ID NO 3
<211> LENGTH: 30
<212> TYPE: DNA
<213> ORGANISM: Artificial sequence
<220> FEATURE:
<223> OTHER INFORMATION: Description of Artificial sequence: synthetic
      oligonucleotide

<400> SEQUENCE: 3
gtttcccgga attcccgttt cagctccttc                                   30

<210> SEQ ID NO 4
<211> LENGTH: 30
<212> TYPE: DNA
<213> ORGANISM: Artificial sequence
<220> FEATURE:
<223> OTHER INFORMATION: Description of Artificial sequence: synthetic
``` oligonucleotide

<400> SEQUENCE: 4
atatctttca gggcatttgg aggtattccg                                                30

<210> SEQ ID NO 5
<211> LENGTH: 5734
<212> TYPE: DNA
<213> ORGANISM: Gluconacetobacter entanii

<400> SEQUENCE: 5

| | | | | | |
|---|---|---|---|---|---|
| catgggcgt | caccccagc | ggccagcttg | gctacctgat | ggacagggcg | ggccttctgc | 60 |
| aagccctcgg | ccactgccat | ctgccgggat | atgaggccaa | atacgaaccg | aaggaaaagc | 120 |
| gcaccttctg | ctaccccacc | cagaacgcca | gcggctgggc | tgtgcagcca | tgatcgccaa | 180 |
| cccctccctc | ttcctgagca | attcggaaga | gcgatttccg | ccgactgaac | acgtcgaaaa | 240 |
| tggcagtttt | ccaccgaaaa | aaggaaagga | ccataggaaa | ggattaatat | cttattttta | 300 |
| tctaggggtt | tgccgatccg | cgattttcgc | tgggaaaccg | ccaaaaatgg | cttgccatta | 360 |
| ggtcgcacca | catgcgacca | taaagtcgca | cagtgtgcga | cctattcggc | ccatatacag | 420 |
| aggttcccca | catgcggaat | gtcacccgtc | tcaagacccg | caaagaccgg | ctccgcgagg | 480 |
| accaagccga | cctgttgaag | caagcccttc | tgcccttcgc | agaggacgat | ggaccgatgc | 540 |
| gggatgcggt | cggacggctc | tacgtccaga | tcaagaacct | caccacccca | gaccccggaa | 600 |
| ccacggagcc | gttcgtcatg | atccgtcccg | cccagaatcg | cgccgtcacc | ctctggctgc | 660 |
| tgaagaacag | taagcggccc | atgaaggccg | tggacgtatg | gacgctgctg | ttcgaccacc | 720 |
| tgtttcccca | taccggccag | atcatgctga | cccgtgagga | aatcgcggaa | aaagtcggta | 780 |
| tccgggtcaa | cgaagttaca | gccgtcatga | acgagctggt | gagcttcggc | gcgattttct | 840 |
| ccgagcgcga | gaaggtggcc | ggaatgcgcg | ggccgggcct | cgcccgctac | tacatgaacc | 900 |
| ggcatgtggc | cgaggtcggc | agccgcgcca | cgcaggaaga | acttgcccta | atcccacgcc | 960 |
| ccggcgccaa | gctggcagtc | gtgcagggtg | gcaaggctta | acccatgaag | gtttcggaac | 1020 |
| tggacgtgtt | cgacagcgcc | aaggcggcac | aagacccgtt | ggtgcgggaa | gaactgctgc | 1080 |
| aagcagcgca | ggcggacggc | cacggccccg | ccctcgctca | tgcccgttcc | gtcatagcca | 1140 |
| aggcgcgggc | cgggcaggac | gccaaggctt | aacggccccg | ccctctcccg | cctcgatccc | 1200 |
| ggcgggcctg | tagcatctcc | tgatgctcct | tggcgttttt | ggcccgctgc | tcggcccgct | 1260 |
| ctttctcggc | cgctgcggct | cttaggcgct | cttcggccag | ccgcatccgc | tcgtccatct | 1320 |
| gacgtttccg | atctgcctcg | gcatccttgg | cggctcctgc | cttcagccct | ttgctgaaag | 1380 |
| ccatccactt | attggcggtt | ttctcggctt | tctgctgtat | cggcggggtc | agccggtcaa | 1440 |
| atgcctgggc | caccctctcg | aagccctcac | gcatggcgtt | gacggcctgc | gccagtttag | 1500 |
| ccagggcgaa | atctatcacc | tcggcccgct | gggcgttctc | ggcccggata | cgccggttgt | 1560 |
| ggttgccggt | cggggtctgg | tggcccttcc | gttccagagc | caccacattc | ggccccatgt | 1620 |
| gccgctctgg | aacgcggtct | agccctgct | ccgcattgct | ccggtgatct | atccgggcct | 1680 |
| cttgcccagc | ccgctctagc | gcggcattgg | caaggcccgc | ccatagctgc | cggatttcct | 1740 |
| tcacctcgtc | ggcggccttc | cccagtccca | tgccctgccg | cttcttgtcg | acagttcga | 1800 |
| tggttgattt | gtctccaaag | gacagcttgc | catcggcccc | ccgctccacc | gtgcgggtgg | 1860 |
| tggtcatgat | gtgcgcgtga | tgattccggt | cgtcgccctc | gtcacccgga | agatgcacgg | 1920 |
| ccacgtccac | ggccaccccg | taccgctgga | ccaactcacg | cgcgaaactg | tccgccagtt | 1980 |

```
cggcccgctg ctcgctggtg agttcatgag ggagggccac aacccattcc ctcccggtgc   2040
gggcgtcctt gcgtttctct gatcgctccg cgtcattcca caattccgaa cggtcagcgg   2100
tgccaccccc cggaatgaaa attgccttat gggcaacgct attctgcctg gggctgtatt   2160
tgtgttcgtg cccgtcaacc tcgttggtca aatcctcgcc agcacgatac gcagccgcag   2220
ccacaacgga acgccctgcg ctccggctga tcggtttcgt ttctgcgcga tagattgcca   2280
cggatcgagc gcctaccttt tggagttaaa cgggggggttc aggggggcga agccaccatg   2340
acgcaggact tgcacttgtg caagtcgtaa ctgcgccctt aatacctgac ggcatcaagg   2400
gatatgtggt attcgtttga aacggaacgg ctccacggtg aggatgatat gagcgatatt   2460
gcgaaagaga ttgagaacgc caaaaggatc atagctgaac agaaaaagcg catcaaagat   2520
gcccagaagg aagcagctaa agcggaatca agttgaggg accgtcagaa ctacatcttg   2580
ggcggcgcac tggtaaaact tgccgaaaca gatgaacggg ccgtccgcac tattgaaaca   2640
cttttgaagc tggtggatcg tccatcagac cggaaggcgt ttgaggtgtt ttcccgtctc   2700
ccatccctct ccctgcccac gcagccagca ccggacaccg gccatgagtg aggcactgga   2760
agaagatccg tttgaactgt tcaaaagggt cgaaaaagc ctgtccacgg ccaccgccag   2820
catggagcgg ctggccgccg aacaagatgc caggtgcaag accatttcag acgccgccgg   2880
aaaagcctct aaattggccg aggaagccgg tgacaccttc acagcatcca agaggcgtct   2940
gatgatctgg acggccctct cgcggctct gctggtctgt ggcgggtggt tggcgggtta   3000
ttggctggga caccgtgacg gttgggcctc tggcacggcc cacgacgtct aagaaaccat   3060
tattatcatg acattaacct ataaaatag gcgtatcacg aggccctttc gtctcgcgcg   3120
tttcggtgat gacggtgaaa acctctgaca catgcagctc ccgagacgg tcacagcttg   3180 tctgtaagcg gatgccggga gcagacaagc ccgtcagggc gcgtcagcgg gtgttggcgg   3240
gtgtcggggc tggcttaact atgcggcatc agagcagatt gtactgagag tgcaccatat   3300
gcggtgtgaa ataccgcaca gatgcgtaag gagaaaatac cgcatcaggc gccattcgcc   3360
attcaggctg cgcaactgtt gggaagggcg atcggtgcgg gcctcttcgc tattacgcca   3420
gctggcgaaa ggggatgtg ctgcaaggcg attaagttgg gtaacgccag gttttccca   3480 gtcacgacgt tgtaaaacga cggccagtgc caagcttgca tgcctgcagg tcgactctag   3540
aggatccccg ggtaccgagc tcgaattcgt aatcatggtc atagctgttt cctgtgtgaa   3600
attgttatcc gctcacaatt ccacacaaca tacgagccgg aagcataaag tgtaaagcct   3660
ggggtgccta atgagtgagc taactcacat taattgcgtt gcgctcactg cccgctttcc   3720
agtcgggaaa cctgtcgtgc cagctgcatt aatgaatcgg ccaacgcgcg gggagaggcg   3780
gtttgcgtat tgggcgctct tccgcttcct cgctcactga ctcgctgcgc tcggtcgttc   3840
ggctgcggcg agcggtatca gctcactcaa aggcggtaat acggttatcc acagaatcag   3900
gggataacgc aggaaagaac atgtgagcaa aaggccagca aaaggccagg aaccgtaaaa   3960
aggccgcgtt gctggcgttt ttccataggc tccgcccccc tgacgagcat cacaaaaatc   4020
gacgctcaag tcagaggtgg cgaaacccga caggactata aagataccag gcgtttcccc   4080
ctggaagctc cctcgtgcgc tctcctgttc cgaccctgcc gcttaccgga tacctgtccg   4140
cctttctccc ttcgggaagc gtggcgcttt ctcaatgctc acgctgtagg tatctcagtt   4200
cggtgtaggt cgttcgctcc aagctgggct gtgtgcacga accccccgtt cagcccgacc   4260
gctgcgcctt atccggtaac tatcgtcttg agtccaaccc ggtaagacac gacttatcgc   4320
```

-continued

```
cactggcagc agccactggt aacaggatta gcagagcgag gtatgtaggc ggtgctacag    4380
agttcttgaa gtggtggcct aactacggct acactagaag gacagtattt ggtatctgcg    4440
ctctgctgaa gccagttacc ttcggaaaaa gagttggtag ctcttgatcc ggcaaacaaa    4500
ccaccgctgg tagcggtggt ttttttgttt gcaagcagca gattacgcgc agaaaaaaag    4560
gatctcaaga agatcctttg atcttttcta cggggtctga cgctcagtgg aacgaaaact    4620
cacgttaagg gattttggtc atgagattat caaaaaggat cttcacctag atccttttaa    4680
attaaaaatg aagttttaaa tcaatctaaa gtatatatga gtaaacttgg tctgacagtt    4740
accaatgctt aatcagtgag gcacctatct cagcgatctg tctatttcgt tcatccatag    4800
ttgcctgact ccccgtcgtg tagataacta cgatacggga gggcttacca tctggcccca    4860
gtgctgcaat gataccgcga gacccacgct caccggctcc agatttatca gcaataaacc    4920
agccagccgg aagggccgag cgcagaagtg gtcctgcaac tttatccgcc tccatccagt    4980
ctattaattg ttgccgggaa gctagagtaa gtagttcgcc agttaatagt ttgcgcaacg    5040
ttgttgccat tgctacaggc atcgtggtgt cacgctcgtc gtttggtatg gcttcattca    5100
gctccggttc ccaacgatca aggcgagtta catgatcccc catgttgtgc aaaaaagcgg    5160
ttagctcctt cggtcctccg atcgttgtca gaagtaagtt ggccgcagtg ttatcactca    5220
tggttatggc agcactgcat aattctctta ctgtcatgcc atccgtaaga tgcttttctg    5280
tgactggtga gtactcaacc aagtcattct gagaatagtg tatgcggcga ccgagttgct    5340
cttgcccggc gtcaatacgg gataataccg cgccacatag cagaacttta aaagtgctca    5400
tcattggaaa acgttcttcg gggcgaaaac tctcaaggat cttaccgctg ttgagatcca    5460
ttcgatgtaa cccactcgtg cacccaactg atcttcagca tcttttactt tcaccagcgt    5520
ttctgggtga gcaaaaacag gaaggcaaaa tgccgcaaaa aagggaataa gggcgacacg    5580
gaaatgttga atactcatac tcttcctttt tcaatattat tgaagcattt atcagggtta    5640
ttgtctcatg agcggataca tatttgaatg tatttagaaa aataaacaaa tagggggttcc    5700
gcgcacattt ccccgaaaag tgccacctga cgtc                                5734
```

<210> SEQ ID NO 6
<211> LENGTH: 30
<212> TYPE: DNA
<213> ORGANISM: Artificial sequence
<220> FEATURE:
<223> OTHER INFORMATION: Description of Artificial sequence: synthetic
      oligonucleotide

<400> SEQUENCE: 6
cgctgacgtc gtgggccgtg ccagaggccc                                      30

<210> SEQ ID NO 7
<211> LENGTH: 30
<212> TYPE: DNA
<213> ORGANISM: Artificial sequence
<220> FEATURE:
<223> OTHER INFORMATION: Description of Artificial sequence: synthetic
      oligonucleotide

<400> SEQUENCE: 7
ggccaagacg tctgcagcat ggggcgtcac                                      30

GENE INVOLVED IN GROWTH-PROMOTING FUNCTION OF ACETIC ACID BACTERIA AND USES THEREOF

The present application claims priority to, and is the National Phase under 35 U.S.C. § 371 of, PCT International Application No. PCT/JP2004/008797, which has an International filing date of Jun 16, 2004, which designated the United States of America. This application further claims priority under 35 U.S.C. § 119 to JP 2003-183047 filed on Jun. 26, 2003. The entire contents of each of these applications is hereby incorporated by reference.

TECHNICAL FIELD

The present invention relates to an acetic acid-resistant microorganism, and more specifically, to a gene encoding a protein having a growth-promoting function derived from a microorganism, a microorganism wherein the number of copies of such gene is amplified, and a method for producing vinegar using such microorganisms.

BACKGROUND ART

Acetic acid bacteria are microorganisms broadly utilized for vinegar production. In particular, acetic acid bacteria belonging to the genus *Acetobacter* and the same belonging to the genus *Gluconacetobacter* are used for industrial acetic acid fermentation.

In acetic acid fermentation, ethanol contained in media is oxidized and converted into acetic acid by acetic acid bacteria. As a result, acetic acid is accumulated in the media. Acetic acid is also inhibitory on acetic acid bacteria. As the amount of accumulated acetic acid increases and the acetic acid concentration in media becomes higher, the growth ability and the fermentation ability of acetic acid bacteria gradually decrease.

In particular, growth induction period, that is, the period until acetic acid bacteria actually start to grow, and then it becomes possible to confirm the accumulation of acetic acid, tends to be longer as the acetic acid concentration becomes higher.

Hence, in acetic acid fermentation, it is desired to further shorten the growth induction period, even in the case of a higher acetic acid concentration. As a means for this purpose, a method has been disclosed that involves adding PQQ (4,5-dihydro-4,5-dioxo-1H-pyrrolo[2,3-f]quinoline-2,7,9-tricarboxylic acid) to a fermentation liquid to promote growth, so as to shorten so-called the growth induction period (e.g., see JP Patent Publication (Kokai) No. 61-58584 A (1986)).

However, obtaining PQQ in large quantities is difficult, and PQQ is expensive. Thus, implementation of such a method at industrial scale has been considered to be uneconomical. Accordingly, efforts have been made to breed and improve acetic acid bacteria by promoting the growth (resistance to acetic acid) of acetic acid bacteria in the presence of a high acetic acid concentration, cloning genes encoding proteins having a function capable of shortening so-called the growth induction period (genes involved in growth promotion), and using the genes involved in growth promotion.

However, no genes involved in growth promotion of acetic acid bacteria have been isolated so far. Under such circumstances, isolation of a novel gene having a growth-promoting function and encoding a protein that has functions to promote at a practical level the growth (resistance to acetic acid) of acetic acid bacteria in the presence of a high acetic acid concentration and to shorten the growth induction period, and generating acetic acid bacteria having a stronger growth function using the gene involved in growth promotion have been desired.

DISCLOSURE OF THE INVENTION

The objects of the present invention are to isolate a novel gene having a growth-promoting function and encoding a protein capable of improving at a practical level a growth function (resistance to acetic acid) in the presence of a high acetic acid concentration and of shortening a so-called growth induction period, to breed an acetic acid bacterium having a better growth-promoting function using the gene having such growth-promoting function, and to provide a method for efficiently producing vinegar with a high acetic acid concentration using the acetic acid bacterium.

We generated a hypothesis that a specific gene encoding a protein having a growth-promoting function that is absent in other microorganisms could be present in acetic acid bacteria that are capable of growing and fermenting even in the presence of acetic acid. We then attempted to isolate such gene and thus have succeeded in isolation of such novel gene. Furthermore, we have obtained findings that the use of such gene encoding a protein having a growth-promoting function enables improvement in the growth-promoting function and the resistance to acetic acid of microorganisms, as well as efficient production of novel vinegar containing acetic acid at a high concentration. Thus, we have completed the present invention.

The present invention is as described in the following (1) to (8).

(1) A protein of the following (A) or (B):
(A) a protein containing the amino acid sequence shown in SEQ ID NO: 2; or
(B) a protein containing an amino acid sequence derived from the amino acid sequence shown in SEQ ID NO: 2 by substitution, deletion, insertion, addition, or inversion of 1 or several amino acids and having a growth-promoting function.

(2) A DNA, which encodes the following protein (A) or (B):
(A) a protein containing the amino acid sequence shown in SEQ ID NO: 2; or
(B) a protein containing an amino acid sequence derived from the amino acid sequence shown in SEQ ID NO: 2 by substitution, deletion, insertion, addition, or inversion of 1 or several amino acids and having a growth-promoting function.

(3) A DNA of the following (A), (B), or (C):
(A) a DNA containing the nucleotide sequence of nucleotide Nos. 180 to 1376 in the nucleotide sequence shown in SEQ ID NO: 1;
(B) a DNA being capable of hybridizing under stringent conditions to a DNA consisting of a sequence complementary to the nucleotide sequence of nucleotide Nos. 180 to 1376 in the nucleotide sequence shown in SEQ ID NO: 1, and encoding a protein having a growth-promoting function; or
(C) a DNA being capable of hybridizing under stringent conditions to a DNA consisting of a nucleotide sequence that is produced from a part of the nucleotide sequence of nucleotide Nos. 180 to 1376 in the nucleotide sequence shown in SEQ ID NO: 1, having a function as a primer or a probe, and encoding a protein having a growth-promoting function.

(4) A recombinant vector, which contains the DNA of (2) or (3) above.

(5) A transformant, which is transformed with the recombinant vector of (4) above.
(6) A microorganism having an enhanced growth-promoting function, wherein the number of copies of the DNA of (2) or (3) above is amplified within a cell.

Examples of the above microorganisms include acetic acid bacteria belonging to the genus *Acetobacter* or the genus *Gluconacetobacter*.

(7) A method for producing vinegar, which comprises culturing the microorganism of (6) above in a medium containing alcohol and causing the microorganism to generate and accumulate acetic acid in the medium.
(8) Vinegar containing acetic acid at a high concentration, which is obtained by the method of (7) above.

BRIEF DESCRIPTION OF THE DRAWINGS

FIG. 3 shows the amino acid sequence (SEQ ID NO: 2) of a protein encoded by a gene that is derived from *Gluconacetobacter entanii* and is involved in a growth-promoting function.

BEST MODE OF CARRYING OUT THE INVENTION

Figure 1:
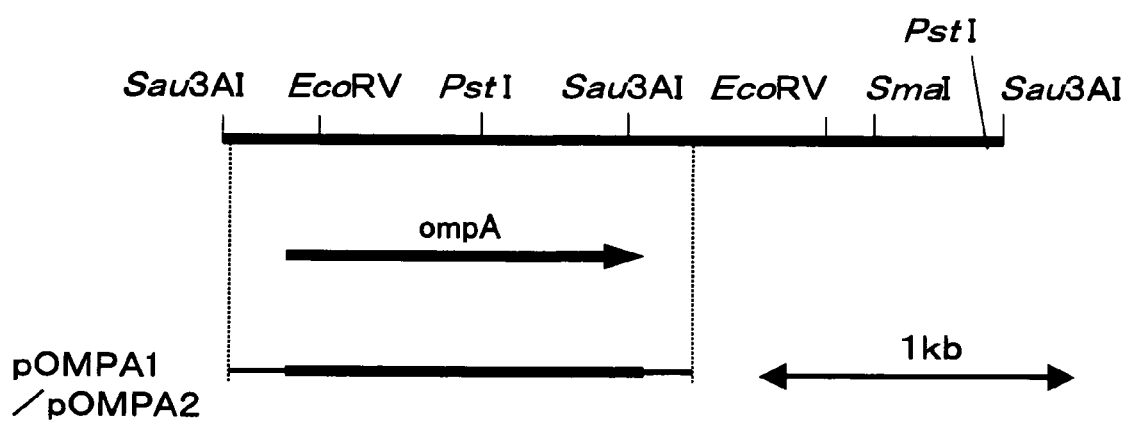
FIG. 1 is a schematic diagram of the restriction enzyme map of a gene fragment (containing pS10 and ompA) derived from *Gluconacetobacter entanii*.

The present invention is described in detail as follows. This application claims a priority from Japanese patent application No. 2003-183047 filed on Jun. 26, 2003, and the content of which described in the specification and/or drawings is herein incorporated.

1. Isolation of a Gene Encoding a Protein Having a Growth-Promoting Function

We have developed a method for isolating a gene having a growth-promoting function from acetic acid bacteria and have attempted to isolate a gene having such function. According to this isolation method, a gene having a growth-promoting function is isolated from acetic acid bacteria by constructing a chromosomal DNA library of acetic acid bacteria, transforming acetic acid bacteria with the chromosomal DNA library, and then screening for an acetic acid bacterial strain capable of growing within 3 days on agar media in the presence of 1% acetic acid, whereas acetic acid bacteria generally require 4 days to grow on the same media.

By the application of this method to acetic acid bacteria belonging to the genus *Gluconacetobacter*, which are actually used for vinegar production, we have succeeded for the first time in cloning a novel gene having a growth-promoting function. The novel gene can improve the growth-promoting function by which a growth function (resistance to acetic acid) is enhanced at a practical level in the presence of a high acetic acid concentration and the growth induction period is shortened.

The thus obtained acetic acid resistance gene has homology to some extent with a group of proteins produced by an ompA gene that has been found in *Escherichia coli*, an ompA gene from *Caulobacter crescentus*, and others, as a result of a homology search of DDBJ/EMBL/Genbank and SWISS-PROT/PIR. It was presumed that the gene is the ompA gene from acetic acid bacteria.

Furthermore, the ompA gene of the present invention has 36% homology at the amino acid sequence level with the ompA gene from *Escherichia coli* and has 30% homology at the amino acid sequence level with the ompA gene from *Caulobacter crescentus*. Because of such extremely low degrees of homology, it was confirmed that the ompA gene of the present invention is somewhat analogous to ompA genes from other microorganisms, but is a novel gene (hereinafter, also referred to as the ompA gene) encoding a novel protein (hereinafter, also referred to as the protein OMPA) specific to acetic acid bacteria.

In the present invention, a transformant having an amplified number of copies of the ompA gene was generated by ligating the ompA gene to a plasmid vector and then transforming an acetic acid bacterium with the vector. In such transformant, resistance to acetic acid was significantly enhanced (see Example 3). Furthermore, when the transformant was cultured with aeration in the presence of ethanol, its ability to ferment acetic acid, and particularly, its growth-promoting function, were significantly enhanced. Growth-promoting function (resistance to acetic acid) in the presence of a high acetic acid concentration was also enhanced. Hence, shortened growth induction period, enhanced growth rate, ability to grow in increased acetic acid concentrations and the like were confirmed (see Examples 2 to 4). Accordingly, it could be confirmed that the ompA gene surely encodes a protein having a growth-promoting function and that the gene is expressed so that the function of the protein can be exerted. Hence, we have expected that vinegar with a high acetic acid concentration can be efficiently produced using a microorganism wherein the number of copies of the ompA gene is amplified.

2. DNA and Protein of the Present Invention

The DNA of the present invention encodes the ompA gene derived from an acetic acid bacterium and encodes a regulatory sequence of the gene. Furthermore, it is presumed that the DNA encodes a protein having a function to improve resistance to acetic acid and a growth-promoting function (SEQ ID NO: 2).

The DNA of the present invention can be obtained from the chromosomal DNA of *Gluconacetobacter entanii* as described below.

First, a chromosomal DNA library of *Gluconacetobacter entanii*, such as the *Acetobacter altoacetigenes* MH-24 strain (deposited under accession number FERM BP-491 on Feb. 23, 1984, (original deposition) with the International Patent Organism Depositary (Tsukuba Central 6, 1-1-1 Higashi Tsukuba, Ibaraki, Japan), the National Institute of Advanced Industrial Science and Technology (AIST)), is prepared. The chromosomal DNA can be obtained by a conventional method (e.g., see JP Patent Publication (Kokai) No. 60-9489 A (1985)).

Next, to isolate the ompA gene, a chromosomal DNA library is constructed from the above-obtained chromosomal DNA. First, the chromosomal DNA is partially digested with appropriate restriction enzymes to obtain a mixture of various fragments. Through the regulation of time for cleavage reaction and the like so as to regulate the degrees of cleavage, wide-ranging types of restriction enzymes can be used. For example, the chromosomal DNA can be digested by applying Sau3A I to the DNA at a temperature of 30° C. or more, preferably at 37° C., at an enzyme concentration ranging from 1 to 10 units/ml for various reaction time (1 minute to 2 hours).

Next, the thus cleaved chromosomal DNA fragments are ligated to a vector DNA that is autonomously replicable within acetic acid bacteria, thereby constructing a recombinant vectors. Specifically, the vector DNA is reacted with a restriction enzyme (e.g., BamH I, which causes the generation of a terminal nucleotide sequence complementary to the restriction enzyme Sau3A I used for the cleavage of the chromosomal DNA) under conditions of a temperature of 30° C. and an enzyme concentration ranging from 1 to 100 units/ml for 1 or more hours, thereby completely digesting and cleaving the vector DNA.

Next, the mixture of chromosomal DNA fragments obtained as described above is mixed with the cleaved vector DNA, and then $T_4$ DNA ligase is added and reacted under conditions in which temperature ranges from 4° C. to 16° C. and enzyme concentration ranges from 1 to 100 units/ml for 1 or more hours (preferably 6 to 24 hours), thereby obtaining a recombinant vector.

Methods for constructing a chromosomal DNA library from chromosomal DNA are known in the art (e.g., the shot gun method), and are not limited to the above method.

An acetic acid bacterium that generally requires 4 days to grow in the presence of 1% acetic acid concentration on an agar medium, such as the *Acetobacter aceti* No. 1023 strain (deposited under accession number FERM BP-2287 on Jun. 27, 1983, (original deposition) with the International Patent Organism Depositary (Tsukuba Central 6, 1-1-1 Higashi, Tsukuba, Ibaraki, Japan), the National Institute of Advanced Industrial Science and Technology) is transformed using the thus obtained recombinant vector. Subsequently, the strains are spread on a 1% acetic acid-containing agar medium, followed by 3 days of culture. The generated colonies are inoculated and cultured in a liquid medium. Plasmids are collected from the thus obtained bacteria, so that DNA fragments containing the ompA gene can be obtained.

A specific example of the DNA of the present invention is a DNA having the nucleotide sequence shown in SEQ ID NO: 1. In such DNA, the nucleotide sequence of nucleotide Nos. 180 to 1376 in SEQ ID NO: 1 is a coding region that encodes the protein shown in SEQ ID NO: 2.

The nucleotide sequence shown in SEQ ID NO: 1 or the amino acid sequence shown in SEQ ID NO: 2 (corresponding to nucleotide Nos. 180 to 1376 of SEQ ID NO: 1 in FIG. 3) showed 36% homology at the amino acid sequence level with the ompA gene from *Escherichia coli* and showed 30% homology at the amino acid sequence level with the ompA gene from *Caulobacter crescentus* as a result of homology search of DDBJ/EMBL/Genbank and SWISS-PROT/PIR. Thus, it was presumed that the relevant gene encodes a protein OMPA. However, because both homologies were as low as 40% or less, it was evident that the gene is a novel gene differing from these genes.

Regarding the DNA of the present invention, the nucleotide sequence of the ompA gene encoded by the DNA has been elucidated here. Thus, the DNA can be obtained by polymerase chain reaction (PCR reaction) using genomic DNA of an acetic acid bacterium, *Gluconacetobacter entanii*, as a template, and oligonucleotides synthesized based on the nucleotide sequence as primers, or by hybridization using an oligonucleotide synthesized based on the nucleotide sequence as a probe, for example. Such DNA having functions as a primer or a probe and prepared from a partial sequence of the ompA gene is also encompassed in the DNA of the present invention. Specifically, DNA conisisting of the sequence shown in SEQ ID NO: 3 or 4 can be used as a primer in the present invention, but the DNA of the present invention is not limited thereto. Here, "having functions as a primer or a probe" means to have the length and nucleotide composition of a nucleotide sequence, which enable use as a primer or a probe. Design of such DNA capable of functioning as a primer or a probe is well-known by persons skilled in the art.

DNA (oligonucleotide) can be synthesized according to a conventional method using various commercially available DNA synthesizers, for example. Furthermore, PCR reaction can be carried out according to a conventional method using Taq DNA polymerase (produced by TAKARA BIO INC.), KOD-Plus- (produced by TOYOBO CO., LTD.), and the like using the Thermal Cycler Gene Amp PCR system 9700 produced by Applied Biosystems.

Furthermore, the OMPA protein of the present invention is encoded by the above DNA and specifically contains the amino acid sequence shown in SEQ ID NO: 2. As long as a protein containing the amino acid sequence shown in SEQ ID NO: 2 retains a growth-promoting function, the amino acid sequence may comprise a mutation such as substitution, deletion, insertion, addition, or inversion in a plurality of, and preferably 1 or several, amino acids.

For example, the protein of the present invention also includes a protein containing an amino acid sequence derived from the amino acid sequence shown in SEQ ID NO: 2 by deletion of 1 to 10 and preferably 1 to 5 amino acids, addition of 1 to 10 and preferably 1 to 5 amino acids, or substitution of 1 to 10 and preferably 1 to 5 amino acids with other amino acids. DNA that encodes such protein containing an amino acid sequence mutated as described above and having a growth-promoting function can also be obtained by a site-directed mutagenesis method; specifically, by altering the nucleotide sequence for deletion, substitution, insertion, addition, or inversion of amino acids at specific sites, for example. Moreover, the DNA altered as described above can also be obtained by a conventionally known treatment to cause mutation.

Furthermore, a variant of the DNA of the present invention encoding a protein having a growth-promoting function can also be synthesized by the site-directed mutagenesis method or the like. In addition, to introduce mutation into the DNA that is a gene, a known technique such as the Kunkel method and the gapped duplex method or modified methods according thereto can be employed. For example, mutation is introduced using a kit for introducing mutation, which uses the site-directed mutagenesis method (e.g., Mutan-K (produced by TAKARA BIO INC.) or Mutan-G (produced by TAKARA BIO INC.)) or the like. Furthermore, mutation can be introduced into a gene, or a chimeric gene can also be constructed by techniques such as error-prone PCR, DNA shuffling, or the like. The error-prone PCR technique and the DNA shuffling techniques are known in the technical field. For example, regarding the error-prone PCR, see Chen K, and Arnold F H. 1993, Proc. Natl. Acad. Sci. U.S.A., 90: 5618-5622, and regarding the DNA shuffling technique, see Stemmer W. P. 1994, Nature, 370: 389-391 and Stemmer W. P., 1994, Proc. Natl. Acad. Sci. U.S.A. 91: 10747-10751.

Here, "growth-promoting function" in the present invention indicates a function to promote the growth of microorganisms in the presence of acetic acid. More specifically, the term means a rapid growth rate or a large amount of growth of bacteria in the presence of acetic acid. Furthermore, the term also indicates a high upper limit of acetic acid concentration, at which growth or acetic acid fermentation is possible. Such "growth-promoting function" can also mean a function to enhance resistance to acetic acid. Whether or not a gene wherein mutation is introduced as described above encodes a protein having such growth-promoting function can be confirmed by determining the presence or the absence of growth in a medium containing acetic acid, as shown in the examples.

Furthermore, it is generally known that the amino acid sequence of a protein and the nucleotide sequence encoding the protein differ slightly among different species, strains, variants, and varieties. DNAs encoding substantially identical proteins can be obtained from all acetic acid bacteria, particularly those of species or strains belonging to the genus *Acetobacter* or the genus *Gluconacetobacter*, as well as variants, and varieties thereof.

Specifically, for example, in the nucleotide sequence shown in SEQ ID NO: 1, a DNA that hybridizes under stringent conditions to a DNA consisting of a part of a nucleotide sequence complementary to the nucleotide sequence consisting of nucleotide Nos. 180 to 1376 or to a DNA consisting of a nucleotide sequence that can be a probe prepared from a part of the DNA of nucleotide Nos. 180 to 1376 and that encodes a protein having a growth-promoting function can be isolated from acetic acid bacteria belonging to the genus *Acetobacter* or the genus *Gluconacetobacter*, mutated acetic acid bacteria belonging to the genus *Acetobacter* or the genus *Gluconacetobacter*, or naturally mutated strains or varieties thereof. In this way, a DNA encoding a protein substantially identical to the aforementioned protein, that is, a protein retaining a growth-promoting function, can also be obtained. The term "stringent conditions" used herein means conditions whereby so-called specific hybrids are formed and non-specific hybrids are not formed. It is difficult to precisely represent such conditions in numerical values. For example, such conditions are conditions wherein nucleic acids sharing high homology, such as 70% or higher homology, hybridize to each other, and nucleic acids sharing homology lower than this level do not hybridize to each other. Other such examples include general washing conditions for hybridization, such as conditions wherein washing is carried out at 60° C. with a salt concentration corresponding to 0.1% SDS in the case of 1×SSC.

3. Acetic Acid-Resistant Microorganism (Microorganism having Enhanced Growth-Promoting Function) of the Present Invention The DNA of the present invention encodes a protein OMPA having a growth-promoting function. By the use of the DNA of the present invention, a microorganism having an enhanced growth-promoting function in the presence of acetic acid, that is, a microorganism having enhanced resistance to acetic acid, can be produced.

The growth-promoting function of a microorganism can be enhanced, for example, by ligating the ompA gene to a recombinant vector and transforming a microorganism with the vector so as to amplify the intracellular number of copies of the gene, or by ligating a structural gene portion of the gene and a promoter sequence that efficiently functions in a microorganism to a recombinant vector and transforming the microorganism with the vector, so as to amplify the number of copies of the gene and to enhance the gene expression.

The recombinant vector of the present invention can be obtained by ligating the DNA encoding the OMPA protein as described in the above section "2. DNA and protein of the present invention" to an appropriate vector. A transformant can be obtained by transforming a host using such recombinant vector of the present invention so that the ompA gene can be expressed.

As a recombinant vector, a phage or a plasmid that is autonomously replicable within hosts can be used. Examples of plasmid DNA include plasmids derived from *Escherichia coli* (e.g., pBR322, pBR325, pUC118, pET16b and so on), plasmids derived from *Bacillus subtilis* (e.g., pUB110, pTP5 and so on), and plasmids derived from yeast (e.g., YEp13, YCp50 and so on). Examples of phage DNA include λ phages (e.g., λgt10, λZAP and so on). Furthermore, a transformant can also be prepared using an animal virus vector such as retrovirus or vaccinia virus, an insect virus vector such as baculovirus, a bacterial artificial chromosome (BAC), yeast artificial chromosome (YAC), or the like.

Furthermore, target DNA can also be introduced into a host using a multi-copy vector, transposon, or the like. In the present invention, such multi-copy vector or transposon is also included in the recombinant vector of the present invention. Such multi-copy vector includes pUF106 (e.g., see Fujiwara, M. et al., Cellulose, 1989, 153-158), pMV24 (e.g., see Fukaya, M. et al., Appl. Environ. Microbiol., 1989, 55: 171-176), pGI18 (e.g., see the specification of JP Patent Application 2003-350265; Example 3), pTA 5001 (A), and pTA 5001 (B) (e.g., see JP Patent Publication (Kokai) No. 60-9488 A (1985)). A chromosome integration-type vector pMVL1 (e.g., see Okumura, H. et al., Agric. Biol. Chem., 1988, 52:3125-3129) can also be used. Moreover, examples of such transposon include Mu and IS1452.

To insert the DNA of the present invention into a vector, a method that involves cleaving purified DNA with an appropriate restriction enzyme and then inserting the resultant into a restriction enzyme site or a multi-cloning site of appropriate vector DNA so as to ligate it to the vector is employed, for example.

The DNA of the present invention should be incorporated into a vector so that the functions of a gene encoded by the DNA are exerted. Hence, in addition to a promoter and the DNA of the present invention, if desired a cis element such as an enhancer, a splicing signal, a polyA addition signal, a selection marker, a ribosome-binding sequence (SD sequence), or the like can be ligated to a recombinant vector of the present invention. Furthermore, examples of such selection marker include a dihydrofolate reductase gene, a kanamycin resistance gene, a tetracycline resistance gene, an ampicillin resistance gene, and a neomycin resistance gene or the like.

Furthermore, to substitute a promoter sequence of the ompA gene on the chromosomal DNA with another promoter sequence capable of efficiently functioning in acetic acid bacteria belonging to the genus *Acetobacter* or *Gluconacetobacter*, a vector for homologous recombination is constructed and then homologous recombination is occurred in the chromosome of a microorganism using the vector. Examples of such promoter sequence include those derived from microorganisms other than acetic acid bacteria, such as a promoter sequence of an ampicillin resistance gene of *Escherichia coli* plasmid pBR322 (produced by TAKARA BIO INC.), that of a kanamycin resistance gene of a plasmid pHSG298 (produced by TAKARA BIO INC.), that of a chloramphenicol resistance gene of a plasmid pHSG396 (produced by TAKARA BIO INC.), and that of a β-galactosidase gene or the like. Construction of a vector for homologous recombination is known by persons skilled in the art. As described above, through arrangement of the endogenous ompA gene in a microorganism under control of a strong promoter, the number of copies of the ompA gene is amplified and thus the expression is enhanced.

Microorganisms to be used for transformation are not specifically limited, as long as they can express introduced DNA. Examples of such microorganisms include bacteria (e.g., *Escherichia coli, Bacillus subtilis*, and lactic acid bacteria), yeast, and fungi such as those belonging to the genus *Aspergillus*. In the present invention, it is preferable to use acetic acid bacteria as the microorganisms used herein because of the purpose of enhancing the growth-promoting function thereof. Among acetic acid bacteria, bacteria belonging to the genus *Acetobacter* and those belonging to the genus *Gluconacetobacter* are preferable.

An example of bacteria belonging to the genus *Acetobacter* is *Acetobacter aceti*. Specifically, for example, the *Acetobacter aceti* No. 1023 strain (FERM BP-2287), the *Acetobacter aceti* subsp. *xylinum* IFO3288 strain, and the *Acetobacter aceti* IFO3283 strain can be used.

Furthermore, examples of bacteria belonging to the genus *Gluconacetobacter* include the *Gluconacetobacter europaeus* DSM6160 strain and *Gluconacetobacter entanii*. Specifically, for example, the *Acetobacter altoacetigenes* MH-24 strain (FERM BP-491) can be used.

Methods for introduction of a recombinant vector into bacteria including acetic acid bacteria are not specifically limited, as long as they are suitable for introducing DNA into bacteria. Examples of such method include a method using a calcium ion (e.g., see Fukaya, M. et al., Agric. Biol. Chem., 1985, 49: 2091-2097) and an electroporation method (e.g., see Wong, H. et al., Proc. Natl. Acad. Sci. U.S.A., 1990, 87: 8130-8134) or the like.

When yeast is used as a host, *Saccharomyces cerevisiae* and *Shizosaccharomyces pombe* are used, for example. Methods for introduction of a recombinant vector into yeast are not specifically limited, as long as they are suitable for introducing DNA into yeast. Examples of such method include an electroporation method, a spheroplast method, and a lithium acetate method.

Transformants can be selected using the properties of a marker gene on a vector to be introduced. For example, when a neomycin resistance gene is used, microorganisms showing resistance to a G418 drug are selected.

In a preferred embodiment of the present invention, a transformant can be obtained by transferring a recombinant vector containing nucleic acids that have at least the nucleotide sequence shown in SEQ ID NO: 1, for example, a recombinant vector pOMPA1, wherein the nucleic acids have been inserted into an acetic acid bacterium-*Escherichia coli* shuttle vector (multi-copy vector) pUF106, into the *Acetobacter aceti* No. 1023 (FERM BP-2287) strain; or by introducing a recombinant vector pOMPA2, wherein the nucleic acids have been inserted into an acetic acid bacterium-*Escherichia coli* shuttle vector (multi-copy vector) pGI18, into the *Acetobacter aceti* subsp. *xylinum* IFO 3288 strain.

When a growth-promoting function is enhanced as described above in acetic acid bacteria belonging to the genus *Acetobacter* or the genus *Gluconacetobacter* having ability to oxidize alcohol, the production amount and production efficiency of acetic acid can be increased.

4. Vinegar Production Method

Microorganisms (acetic acid bacteria) having a selectively enhanced growth-promoting function (as a result of the amplification of the number of copies of a gene having such growth-promoting function) and having ability to oxidize alcohol are produced as described in the above section "3. Acetic acid-resistant microorganism of the present invention." Such microorganisms can be used for producing vinegar, because they can grow in the presence of acetic acid and produce acetic acid. Hence, microorganisms having amplified copy number of the ompA gene are cultured in a medium containing alcohol and then caused to produce and accumulate acetic acid in the medium, so that vinegar containing acetic acid at a high concentration can be efficiently produced.

Acetic acid fermentation in the production method of the present invention may be carried out in a manner similar to a vinegar production method involving a conventional fermentation method using acetic acid bacteria, but a method for fermentation is not specifically limited thereto. A medium to be used for acetic acid fermentation may be either a synthetic or a natural medium as long as it contains a carbon source, a nitrogen source, an inorganic substance, and ethanol, and, if necessary, contains appropriate amounts of nutrition sources required for the growth of the employed microbial strain.

Examples of a carbon source include various carbohydrates such as glucose and sucrose and various organic acids. As a nitrogen source, a natural nitrogen source such as peptone or lysate of the fermentation microorganisms can be used.

Furthermore, culture is carried out under aerobic conditions such as those of a static culture method, a shaking culture method, or an aeration and agitation culture method. Culture is carried out generally at 30° C. The pH for a medium generally ranges from 2.5 to 7 and preferably ranges from 2.7 to 6.5. The pH can also be adjusted using various acids, various bases, buffers, and the like. Culture is generally carried out for 1 to 21 days.

Through culture of microorganisms having an amplified number of copies of the ompA gene, acetic acid is accumulated at a high concentration in a medium. Furthermore, the growth rate of such microorganisms is improved, so that the acetic acid production rate becomes improved.

According to the present invention, a growth-promoting function can be conferred to microorganisms so as to enhance the growth thereof. Furthermore, in microorganisms having ability to oxidize alcohol and particularly in acetic acid bacteria, the growth function (resistance to acetic acid) in the presence of a high acetic acid concentration is enhanced and the growth induction period is significantly shortened. Thus, ability to efficiently accumulate acetic acid at a high concentration in a medium can be conferred to such microorganisms and such bacteria. The thus generated microorganisms (acetic acid bacteria) are useful in production of vinegar containing acetic acid at a high concentration.

EXAMPLES

The present invention will be further described specifically by referring to examples. However, the technical scope of the present invention is not limited by these examples.

Example 1

Cloning of a Gene Derived from *Gluconacetobactor entanii* having a Growth-Promoting Function and Determination of the Nucleotide Sequence and the Amino Acid Sequence thereof (1) Construction of Chromosomal DNA Library The *Acetobacter altoacetigenes* MH-24 strain (FERM BP-491), which is a strain of *Gluconacetobacter entanii*, was cultured in shaking culture at 30° C. in a YPG medium (3% glucose, 0.5% yeast extract, and 0.2% polypeptone) supplemented with 6% acetic acid and 4% ethanol. After the cultivation, the culture medium was centrifuged (7,500×g for 10 minutes), thereby obtaining bacterial cells. From the thus obtained bacterial cells, chromosomal DNAs were prepared according to a chromosomal DNA preparation method (e.g., see JP Patent Publication (Kokai) No. 60-9489 A (1985)).

The chromosomal DNAs obtained in the above manner were partially digested with a restriction enzyme Sau3A I (from TAKARA BIO INC.). *Escherichia coli*-acetic acid bacterium shuttle vector pUF106 was completely digested and cleaved with a restriction enzyme BamH I. Appropriate amounts of these DNAs were mixed in and then ligated using a ligation kit (TaKaRa DNA Ligation Kit Ver. 2, from TAKARA BIO INC.), thereby constructing a chromosomal DNA library of *Gluconacetobacter entanii*.

(2) Cloning of a Gene having a Growth-Promoting Function

The chromosomal DNA library of *Gluconacetobacter entanii* obtained as described above was transformed into the *Acetobacter aceti* No. 1023 strain (FERM BP-2287) that is known to generally require 4 days to grow on an agar medium containing 1% acetic acid. The bacterial cells were then cultured on a YPG agar medium containing 1% acetic acid and 100 µg/ml ampicillin at 30° C. for 3 days. Colonies generated within 3 days were inoculated and cultured on a YPG medium containing 100 µg/ml ampicillin and then plasmids were collected from the obtained bacterial cells. An approximately 2.3-kbp Sau3A I fragment was cloned as shown in FIG. 1, and the plasmid was named pS10.

As described above, a gene fragment was obtained that has a growth-promoting function enabling the *Acetobacter aceti* No. 1023 strain to grow within 3 days on an agar medium containing 1% acetic acid, although the strain generally requires 4 days to grow on such an agar medium containing 1% acetic acid.

(3) Determination of the Nucleotide Sequence of the Cloned DNA Fragment

The above cloned Sau3A I fragment was inserted into the BamH I site of pUC19, and then the nucleotide sequence of the fragment was determined by Sanger's dideoxy chain termination method. As a result, the nucleotide sequence shown in SEQ ID NO: 1 was determined. Sequencing was carried out for the entire region of both DNA strands with all the cleavage points overlapping each other. The thus obtained gene was named ompA.

In the nucleotide sequence shown in SEQ ID NO: 1, the presence of an open reading frame encoding 399 amino acids shown in SEQ ID NO: 2 (FIG. 3) ranging from nucleotide Nos. 180 to 1376 was confirmed.

Example 2

Effect of Shortening the Growth Induction Period in a Transformant with a Gene having a Growth-Promoting Function from *Gluconacetobacter entanii*

(1) Transformation into *Acetobacter aceti*

The above ompA gene cloned according to Example 1 from the *Acetobacter altoacetigenes* MH-24 strain (FERM BP-491) was amplified by the PCR method using KOD-Plus- (from TOYOBO CO., LTD.). The thus amplified DNA fragment was inserted into the restriction enzyme Sma I cleavage site of the acetic acid bacterium—*Escherichia coli* shuttle vector pUF106 (e.g., see Fujiwara, M. et al., CELLULOSE, 1989, 153-158), so as to prepare a plasmid pOMPA1. The amplified fragment inserted in pOMPA1 is schematically shown in FIG. 1. FIG. 1 shows the restriction enzyme map of the *Gluconacetobacter entanii*-derived gene fragment (pS10) cloned using Sau3A I, the position of the gene having the growth-promoting function, and the fragment inserted into pOMPA1.

The PCR method was carried out as described in detail below. Specifically, PCR was carried out under the following PCR conditions using a genomic DNA of the *Acetobacter altoacetigenes* MH-24 strain as a template, primer 1 (5'-GTTTCCCGGAATTCCCGTTTCAGCTCCTTC-3': SEQ ID NO: 3), primer 2 (5'-ATATCTTTCAGGGCATTTGGAGGTATTCCG-3': SEQ ID NO: 4), and KOD-Plus- (from TOYOBO CO., LTD.).

Specifically, the PCR method was carried out for 30 cycles, each comprising 94° C. for 15 seconds, 60° C. for 30 seconds, and 68° C. for 1 minute.

The pOMPA1 was transformed into the *Acetobacter aceti* No. 1023 strain by an electroporation method (e.g., see Wong, H C. et al., Proc. Natl. Acad. Sci. U.S.A., 1990, 87: 8130-8134). The transformant was selected using a YPG agar medium supplemented with 100 µg/ml ampicillin and 1% acetic acid.

Plasmids were extracted from the ampicillin-resistant transformant that had grown on the selection medium within 3 days and then analyzed according to a conventional method. Thus, it was confirmed that the strain retained plasmids having the gene with the growth-promoting function.

(2) Acetic Acid Fermentation Test using the Transformant

The ampicillin-resistant transformant obtained as described above having the plasmid pOMPA1 and the original *Acetobacter aceti* No. 1023 strain having only the shuttle vector pUF106 were compared in terms of acetic acid fermentation ability.

Specifically, aeration and agitation culture was carried out in a 2.5 L YPG medium containing 1% acetic acid, 4% ethanol, and 100 µg/ml ampicillin at 30° C., 400 rpm, and 0.20 vvm using a 5 L mini-jar fermentor (from Mitsuwa Scientific Corp.; KMJ-5A). The strains were allowed to ferment to an acetic acid concentration of 3%. Subsequently, some of the culture medium was removed, with 700 mL of the culture medium left in the mini-jar fermentor. A 1.8 L YPG medium containing acetic acid, ethanol, and 100 µg/ml ampicillin was added to the remaining 700 ml of the culture medium to an acetic acid concentration of 3% and an ethanol concentration of 4%. Acetic acid fermentation was initiated again. Aeration and agitation culture was continued while adding ethanol so as to maintain the ethanol concentration of 1% in the medium. The transformant was compared with the original strain in terms of acetic acid fermentation ability. The results are summarized in Table 1.

TABLE 1

| | Final acetic acid concentration achieved (%) | Specific growth rate (OD660/hr) | Production rate (%/hr) | Growth induction period (hr) |
|---|---|---|---|---|
| Original strain | 9.9 | 0.0162 | 0.071 | 54.4 |
| Transformant | 9.8 | 0.0213 | 0.072 | 5.0 |

Based on the results in Table 1, it can be confirmed that in the case of the transformant, the specific growth rate was significantly higher, the growth induction period was significantly shortened, and the transformant was able to efficiently conduct acetic acid fermentation.

Example 3

Enhancement of Acetic Acid Resistance of the Transformant with a Gene having a Growth-Promoting Function from *Gluconacetobacter entanii*

(1) Construction of Acetic Acid Bacterium-*Escherichia Coli* Shuttle Vector pGI18 pGI18 was constructed using an approximately 3.1-kb plasmid pGI1 derived from the *Acetobacter altoacetigenes* MH-24 strain (FERM BP-491) and pUC18.

Specifically, bacterial cells were collected from the culture medium of the *Acetobacter altoacetigenes* MH-24 strain (FERM BP-491), lysed using sodium hydroxide or sodium dodecyl sulfate, treated with phenol, and then treated with ethanol, thereby purifying plasmid DNA.

The thus obtained plasmid was a circular double-stranded DNA plasmid having 3 recognition sites for Hinc II and 1 recognition site for Sfi I. The entire length of the plasmid was approximately 3100 base pairs (bp). Furthermore, the plasmid did not have recognition sites for EcoR I, Sac I, Kpn I, Sma I, BamH I, Xba I, Sal I, Pst I, Sph I, or Hind III. The plasmid was named pGI1 and used for the construction of the vector pGI18.

The above-obtained plasmid pGI1 was amplified by the PCR method using KOD-Plus- (from TOYOBO CO., LTD.). The amplification products were cleaved with Aat II. The fragment was inserted into the restriction enzyme Aat II cleavage site of pUC18, thereby preparing a plasmid pGI18 (FIG. 4).

The PCR method was carried out as described in detail below. Specifically, PCR was carried out under the following PCR conditions using a plasmid pGI1 as a template and primer A (SEQ ID NO: 6) and primer B (SEQ ID NO: 7), which have restriction enzyme Aat II recognition sites, as primers.

Specifically, the PCR method was carried out for 30 cycles, each comprising 94° C. for 30 seconds, 60° C. for 30 seconds, and 68° C. for 3 minutes.

Figure 4:
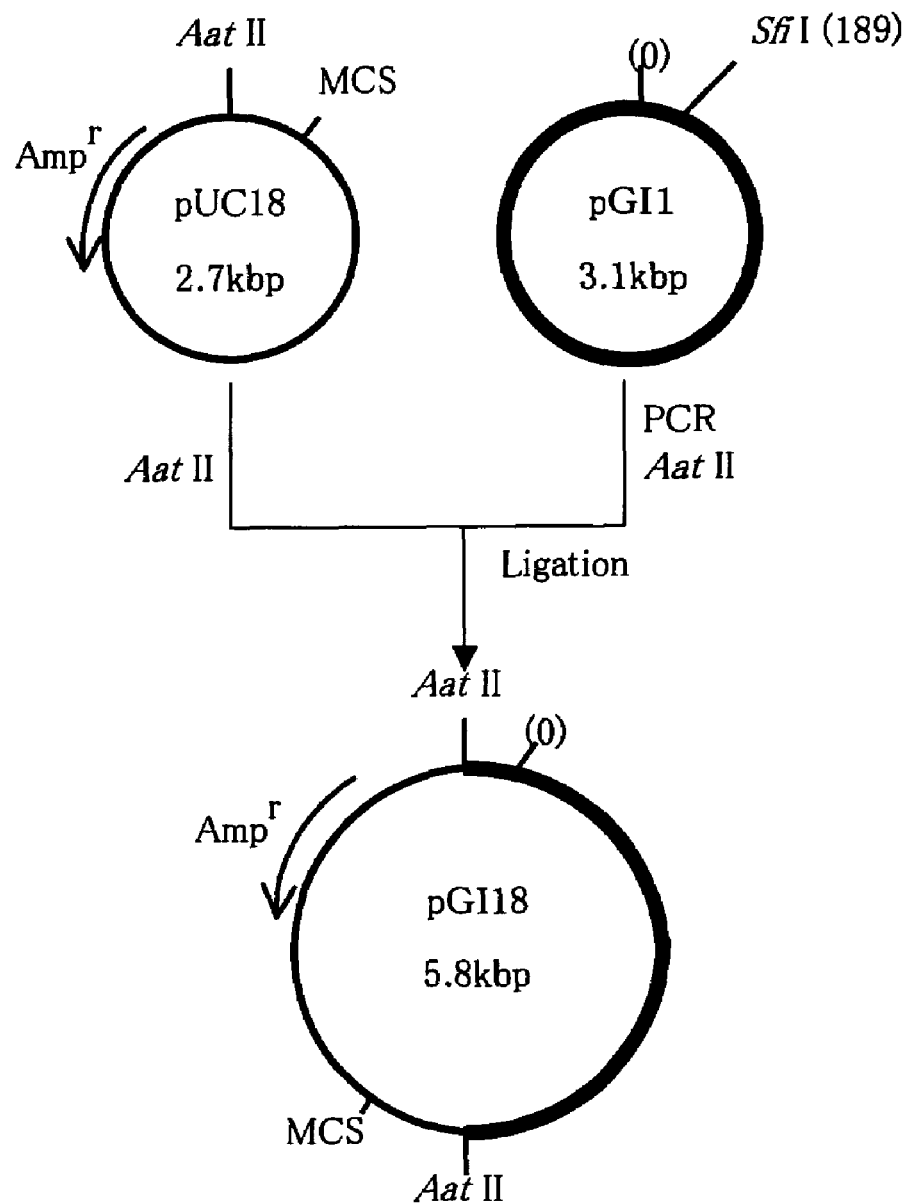
FIG. 4 shows the construction scheme and the restriction enzyme map for pGI18.

As shown in FIG. 4, the thus obtained plasmid pGI18 contained both pUC18 and pGI1, and the entire length thereof was approximately 5800 base pairs (5.8 kbp).

The nucleotide sequence of the plasmid pGI18 is shown in SEQ ID NO: 5.

(2) Transformation into *Acetobacter aceti* subsp. *xylinum*

The gene derived from the *Acetobacter altoacetigenes* MH-24 strain (FERM BP-491) having the growth-promoting function obtained in Example 1 was amplified by the PCR method using KOD-Plus- (from TOYOBO CO., LTD.). The acetic acid bacterium-*Escherichia coli* shuttle vector pGI18 constructed in (1) was cleaved with a restriction enzyme Sma I. The amplified DNA fragment was then inserted into the restriction enzyme Sma I cleavage site of the shuttle vector, so as to prepare a plasmid pOMPA2. The amplified fragment inserted in pOMPA2 is schematically shown in FIG. 1. FIG. 1 shows the restriction enzyme map of the *Gluconacetobacter entanii*-derived gene fragment (pS10) cloned using Sau3A I, the position of the gene having the growth-promoting function, and the fragment inserted into pOMPA2.

The PCR method was carried out as described in detail below. Specifically, PCR was carried out under the following PCR conditions using a genomic DNA of the *Acetobacter altoacetigenes* MH-24 strain as a template, primer 1 (5'-GTTTCCCGGAATTCCCGTTTCAGCTCCTTC-3': SEQ ID NO: 3), primer 2 (5'-ATATCTTTCAGGGCATTTGGAG-GTATTCCG-3': SEQ ID NO: 4), and using KOD-Plus- (from TOYOBO CO., LTD.).

Specifically, the PCR method was carried out for 30 cycles, each comprising 94° C. for 15 seconds, 60° C. for 30 seconds, and 68° C. for 1 minute.

The pOMPA2 was transformed into the *Acetobacter aceti* subsp. *xylinum* IFO3288 strain, which is a strain of *Acetobacter aceti* subsp. *Xylinum*, by the electroporation method (e.g., see Wong, H C. et al., Proc. Natl. Acad. Sci. U.S.A., 1990, 87:8130-8134). The transformant was selected using a YPG agar medium supplemented with 100 μg/ml ampicillin and 1% acetic acid.

Plasmids were extracted from the ampicillin-resistant transformant that had grown on the selection medium and then analyzed according to a conventional method. Thus, the retention of plasmids having the acetic acid resistance gene was confirmed.

(3) Resistance of the Transformant to Acetic Acid

The ampicillin-resistant transformant having the plasmid pOMPA2 obtained in (2) above was compared with the original *Acetobacter aceti* subsp. *xylinum* IFO3288 strain having only the shuttle vector pGI18 introduced therein in terms of growth in a YPG medium supplemented with acetic acid.

Specifically, shaking culture (150 rpm) was carried out at 30° C. in 100 ml of a YPG medium containing 3% acetic acid and 100 μg/ml ampicillin. The growth of the transformant and that of the original strain in the medium supplemented with acetic acid were compared by measuring bacteria concentrations at 660 nm.

Figure 2:
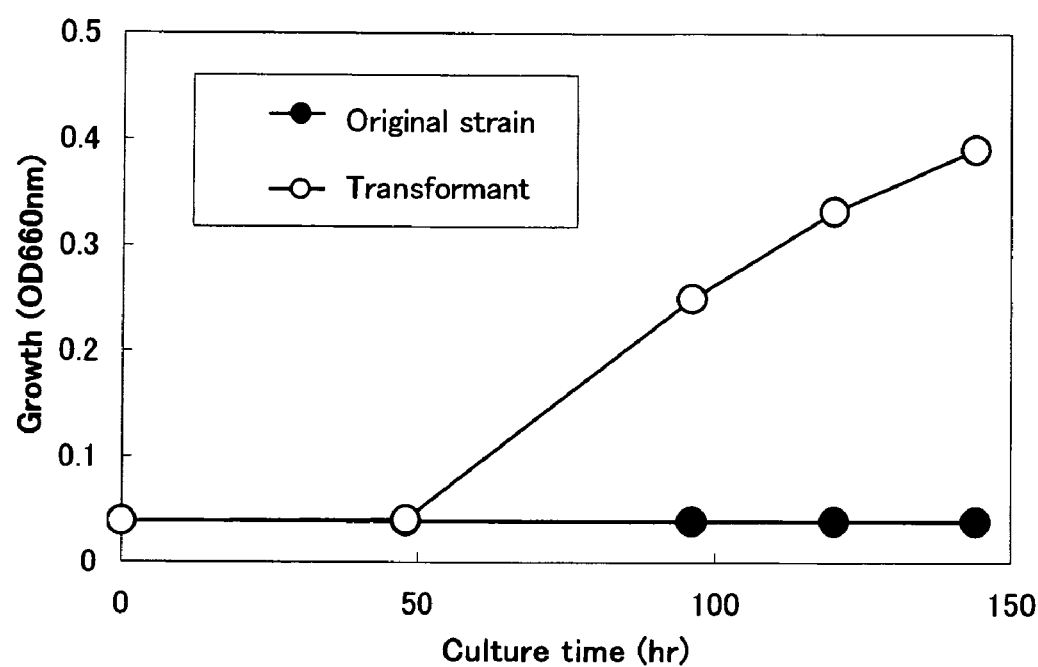
FIG. 2 shows the process of culturing a transformant in a medium containing acetic acid, which has an amplified number of copies of a gene that is derived from *Gluconacetobacter entanii* and has a growth-promoting function.

As a result, as shown in FIG. 2, in the medium supplemented with 3% acetic acid, it could be confirmed that whereas the transformant (indicated with open circles) could grow, the original *Acetobacter aceti* subsp. *xylinum* IFO3288 strain (indicated with closed circles) was unable to grow. Thus, the function to enhance resistance to acetic acid of the gene having the growth-promoting function could be confirmed.

Example 4

Acetic Acid Fermentation Test for the Transformant with a Gene having a Growth-Promoting Function from *Gluconacetobacter entanii*

The ampicillin-resistant transformant having the plasmid pOMPA2 obtained in Example 3 was compared with the original *Acetobacter aceti* subsp. *xylinum* IFO3288 strain having only the shuttle vector pGI18 introduced therein in terms of ability to ferment acetic acid.

Specifically, a 5 L mini-jar fermentor (from Mitsuwa Scientific Corp.; KMJ-5A) was filled with a YPG medium having an acetic acid concentration of 1% and an alcohol concentration of 4%. The transformant or the original strain was inoculated at 0.4% onto the medium. Aeration and agitation culture was then initiated at a fermentation temperature of 32° C., 500 rpm, and 0.20 vvm. When the acetic acid concentration increased to 4% as fermentation proceeded, addition of a raw-material medium (alcohol concentration of 7.8% and acetic acid concentration of 0.26%), which had been prepared by mixing a 17.9% solution of saccharified rice, a 3.2% acetic acid fermentation solution, 7.8% alcohol, and 71.1% water, was initiated. Fermentation was further continued until the acetic acid concentration was increased to 7.2%.

When acetic acid concentration was increased to 7.2%, continuous fermentation was carried out while adjusting the addition rate of the raw-material medium so as to be able to maintain the acetic acid concentration.

In terms of the addition rate of the raw-material medium, that is, addition rate (proportional to production rate), the transformant and the original strain were compared. The results are shown in Table 2.

Moreover, the transformant and the original strain were also compared in terms of acetic acid fermentation ability, when the addition rate in the case of the transformant was adjusted to be almost equivalent to that of the original strain at the time of continuous fermentation at an acetic acid concentration of 7.2%. The results are shown in Table 3.

TABLE 2

|  | Acetic acid concentration (%) | Bacteria concentration (OD660) | Addition rate (g/hr) |
|---|---|---|---|
| Original strain | 7.17 | 0.675 | 87.2 |
| Transformant | 7.23 | 0.675 | 98.5 |

TABLE 3

|  | Acetic acid concentration (%) | Bacteria concentration (OD660) | Addition rate (g/hr) |
|---|---|---|---|
| Original strain | 7.24 | 0.712 | 87.1 |
| Transformant | 7.64 | 0.695 | 91.1 |

Based on the results in Table 2, it was shown that also in the case of continuous acetic acid fermentation, productivity (addition rate of the raw-material medium) was higher and better in the case of the transformant compared with the original strain.

Furthermore, based on the results in Table 3, it was revealed that when continuous acetic acid fermentation was carried out at constant productivity (addition rate of the raw-material medium), the transformant could perform continuous acetic acid fermentation with a higher acetic acid concentration and had better resistance to acetic acid compared with the original strain.

INDUSTRIAL APPLICABILITY

The present invention provides a novel gene having a growth-promoting function. A strain that can be obtained through the use of the gene has an enhanced growth function (resistance to acetic acid) in the presence of a high acetic acid concentration, a shortened growth induction period, and improved resistance to acetic acid. Such strain can be used for highly efficient production of vinegar with a high acetic acid concentration. Hence, the present invention is useful in the highly efficient production of vinegar with a high acetic acid concentration.

All publications, patents, and patent applications cited herein are incorporated herein by reference in their entirety.

Sequence Free Text

SEQ ID NOS: 3, 4, 6, and 7: synthetic oligonucleotides

The invention claimed is:

1. An isolated DNA, which encodes a protein comprising the amino acid sequence according to SEQ ID NO:2.

2. An isolated DNA comprising the nucleotide sequence of nucleotide Nos. 180 to 1376 in the nucleotide sequence shown in SEQ ID NO: 1.

3. A recombinant vector, which comprises the DNA according to claim 1 or 2.

4. A transformant, which is an acetic acid bacterium belonging to the genus *Acetobacter* or the genus *Gluconacetobacter* transformed with the recombinant vector according to claim 3.

5. A method for producing vinegar, which comprises culturing the transformant according to claim 4 in a medium containing alcohol and causing the transformant to generate and accumulate acetic acid in the medium.

* * * * *